| United States Patent [19] | [11] Patent Number: 4,935,244 |
|---|---|
| Clark | [45] Date of Patent: Jun. 19, 1990 |

[54] NEDOCROMIL SODIUM COMPOSITIONS AND METHODS FOR THEIR PREPARATION

[75] Inventor: Andrew R. Clark, Loughborough, England

[73] Assignee: Fisons plc, Ipswich, England

[21] Appl. No.: 272,706

[22] Filed: Nov. 17, 1988

[30] Foreign Application Priority Data

Nov. 25, 1987 [GB] United Kingdom ............... 8727590

[51] Int. Cl.$^5$ ................................................ A61K 37/22
[52] U.S. Cl. .................................... 424/450; 514/291; 264/4.1; 264/4.3
[58] Field of Search ................ 424/450; 546/89; 514/291; 264/4.1, 4.3

[56] References Cited

U.S. PATENT DOCUMENTS

| 4,356,181 | 10/1982 | Payling et al. | 546/89 |
|---|---|---|---|
| 4,614,802 | 9/1986 | Wright | 546/89 |
| 4,760,072 | 7/1988 | Brown et al. | 546/89 |

*Primary Examiner*—Ellis P. Robinson
*Assistant Examiner*—P. L. Prater
*Attorney, Agent, or Firm*—Marshall, O'Toole, Gerstein, Murray & Bicknell

[57] ABSTRACT

There is described a pharmaceutical composition comprising nedocromil sodium and liposomes.

There is also described an aqueous suspension comprising nedocromil sodium partitioned between a free aqueous phase and a liposome phase.

There are also described a method of making the compositions and their use in the manufacture of a medicament for the treatment of reversible obstructive airways disease.

9 Claims, No Drawings

NEDOCROMIL SODIUM COMPOSITIONS AND METHODS FOR THEIR PREPARATION

This invention relates to pharmaceutical compositions comprising nedocromil sodium and methods for their preparation.

Nedocromil sodium is the disodium salt of 9-ethyl-6,9-dihydro-4,6-dioxo-10-propyl-4H-pyrano[3,2-g]quinoline-2,8-dicarboxylic acid. Nedocromil sodium is disclosed in British Patent Specification No: 2022078 and is useful, inter alia, in the treatment of reversible obstructive airways disease. Nedocromil sodium is the disodium salt of a highly water soluble, hydrophilic diacid. Thus, formulations comprising non-aqueous carriers present a considerable problem.

However, we have now surprisingly found a new pharmaceutical composition comprising nedocromil sodium which is of longer duration of action than conventional formulations.

According to the invention there is provided a pharmaceutical composition comprising nedocromil sodium in a liposome entrapped form.

The initial stages of preparation of the composition according to the invention may conveniently follow procedures described in the art. The choice of procedure will depend to some extent on the proposed target organ for the composition, the desired release characteristics and the desired dosing schedule.

One preferred method for preparing drug-containing liposomes is the reverse phase evaporation method. In this method, a solution of liposome-forming lipids is mixed with a smaller volume of an aqueous medium and the mixture is dispersed to form a water-in-oil emulsion. Nedocromil sodium may then be added either to the lipid solution or to the aqueous medium. Removal of the lipid solvent by evaporation gives an aqueous suspension of liposomes. The reverse phase evaporation vesicles (REVs) produced by this method have typical average sizes between about 2-4 microns and are predominantly oligolamellar, that is contains one or a few bilayer shells.

In a second preferred method for preparing drug-containing liposomes, a thin lipid film is hydrated to produce multilamellar vesicles (MLVs). The thin lipid film is produced by dissolving one or more liposome forming lipids in a suitable solvent and evaporating in a flask. The thin film produced is then covered by an aqueous solution of nedocromil sodium, the lipid film hydrating to form MLVs. Typically, the MLVs have sizes between about 0.1 and 10 microns. In general, the percent of total nedocromil sodium which can be encapsulated in the MLVs calculated as the ratio of encapsulated drug to total drug used in vesicle preparation is typically between about 0.1-50% w/w.

The desired size of the liposomes will depend on, inter alia, the desired target organ for the composition and the mode of administration. In general, when the liposomes are intended for administration to the lungs, e.g. via inhalation of an aerosol cloud, the liposomes preferably have a diameter of between 100 nm and 10 $\mu$m. It is known, for example, that liposomes having a diameter of up to 5000 nm may be readily phagocytosed. It is preferred that the liposomes are fractionated to remove substantially all those having a diameter less than 100 nm, and preferably also those having a diameter less than 1 $\mu$m. Fractionation may conveniently be effected by column gel chromatography, for example using cross linked dextran or agarose, the size of the gel being selected according to the desired liposome size. Alternatively, the liposomes may be fractionated using ultracentrifugation, or by dialysis or filtration, e.g. using polycarbonate membrane filtration.

We further provide a pharmaceutical composition according to the invention wherein from 0.1% to 50% w/w of nedocromil sodium to lipid is entrapped, preferably 10% to 45% w/w, more preferably 20% to 45% w/w, most preferably 22% to 45% w/w and especially 22% to 40% w/w, e.g. 37% w/w.

The initial concentration of aqueous nedocromil sodium solution may comprise from 0.1% to 40% w/v of nedocromil sodium preferably from 4% to 32% w/v, more preferably 4% to 16% w/v and most preferably 8% to 16% w/v. Thus the concentration of the entrapped solution may be from 0.1% to 40% w/v of nedocromil sodium, preferably from 4% to 32% w/v, more preferably 4% to 16% w/v and preferably 8% to 16% w/v.

A wide variety of lipid materials may be used to form the liposomes including natural lecithins, e.g. those derived from egg and soya bean, and synthetic lecithins. Lipids which are non-immunogenic and bio-degradable are preferred. The properties of the lipid, for example its phase transition temperature, can have a marked effect on the retention and uptake of the liposomes in the target organ and for this reason the well defined synthetic lecithins are preferred to the natural lecithins. Examples of synthetic lecithins which may be used, together with their respective phase transition temperatures, are di-(tetradecanoyl)phosphatidylcholine (DTPC) (23° C.), di-(hexadecanoyl)phosphatidylcholine (DHPC) (41° C.) and di-(octadecanoyl)phosphatidylcholine (DOPC) (55° C.). We prefer to use di-(hexadecanoyl)phosphatidylcholine as the sole or major lecithin, optionally together with a minor proportion of the di-(octadecanoyl) or the di-(tetradecanoyl) compound. Other synthetic lecithins which may be used are unsaturated synthetic lecithins, for example di-(oleyl)phosphatidylcholine and di-(linoleyl)phosphatidylcholine. We prefer the synthetic lecithin, or the mixture of lipids, to have a phase transition temperature in the range 35°-45° C. In addition to the main liposome-forming lipid or lipids, which are usually phospholipids, other lipids (e.g. in a proportion of 5-40% w/w of the total lipids) may be included, for example cholesterol or cholesterol stearate, to modify the structure of the liposome membrane, rendering it more fluid or more rigid depending on the nature of the main liposome-forming lipid or lipids. An optional third component is a material which provides a negative charge, for example phosphatidic acid, dicetyl phosphate or beef brain ganglioside, or one which provides a positive charge for example stearylamine acetate or cetylpyridinium chloride. The charged component may be included in a proportion of 1-20% w/w of the total lipids.

A wide range of proportions of nedocromil sodium to lipid during formation may be used depending on the lipid and the conditions used. However we have in general found that a range of one part by weight of nedocromil sodium to from 0.01 to 100, preferably 0.05 to 20, most preferably 0.1 to 10 parts by weight of lipid is appropriate.

We prefer the aqueous phase to contain less than 20 ppm of metal ions in group IIa, Ib, IIb and IVb of the periodic table, and of the transition metals, in particular $Pb^{++}$, $Ca^{++}$, $Mg^{++}$, $Fe^{++}$, $Fe^{+++}$ and $Zn^{++}$ ions.

The aqueous phase may be made isotonic, using sodium chloride. In addition the aqueous phase may contain potassium chloride.

The aqueous phase may be adjusted to a pH of between 6 and 8, and preferably 6.5 to 7.5 by the addition of acid or base as appropriate, or by the addition of a suitable buffering agent, e.g. tris(hydroxymethyl)methanamine (Tris).

We prefer the liposome formulation to have a half life (efflux rate) at 37° C. of from about 12 to 48 and preferably 12 to 24 hours. Half lives may be measured using conventional techniques, e.g. by dilution methods. The half life of the formulation may be varied by varying the proportion of the various lipids used to make the liposome.

The compositions of the invention may be used as eye drops in the treatment of allergic eye conditions, e.g. vernal kerato conjunctivitis, the occular symptoms of hay fever and/or marginal infiltration.

The composition may also be used in the treatment of diseases of the gastro-intestinal tract, e.g. ulcerative colitis, and food allergies, by oesophageal administration. Enemas incorporating the compositions may be used in the treatment of bowel diseases, particularly of allergic origin. The compositions may also be used in the treatment of hay fever, by administration to the nose, e.g. as a nasal spray, and in the treatment of skin conditions, e.g. chronic dermatoses in mammals, notably man.

The compositions of the invention may especially be used for the treatment of reversible obstructive airways disease, e.g. by instilling a nebulised aqueous suspension of the nedocromil sodium liposomes into the lungs.

The composition may be in a dry form, e.g. in the form of a freeze dried powder. However, we prefer the composition to be a suspension of liposomes, in particular an aqueous suspension.

We further provide an aqueous suspension of liposomes according to the invention comprising from 5% to 80% w/v liposomes, preferably from 10% to 60% w/v liposomes, more preferably from 20% to 50% w/v liposomes, most preferably from 30% to 50% w/v liposomes and especially 40% w/v liposomes.

When the composition is an aqueous suspension of liposomes, the nedocromil sodium may be partitioned between a free, aqueous phase and an entrapped liposome phase. We find that these aqueous compositions have useful and unexpected properties, in that the aqueous phase can provide an initial 'priming' dose of nedocromil sodium and the liposome phase can provide a maintenance dose of nedocromil sodium.

According to the invention we further provide a pharmaceutical composition comprising an aqueous suspension containing nedocromil sodium partitioned between a free aqueous phase and an entrapped liposome phase.

It is a further feature of the invention to provide an aqueous solution of nedocromil sodium which may be substantially entrapped in a liposome phase having a total concentration of from 0.01% to 30% w/v, preferably from 0.8% to 26% w/v, more preferably 0.8% to 13% w/v and most preferably from 1.6% to 8.0% w/v, e.g. 3.2% w/v or 6.4% w/v.

We prefer the percentage of nedocromil sodium associated with the liposomes to be from 2 to 35% w/w, e.g. from 4 to 25%. The percentage of nedocromil sodium associated with the liposomes can be determined by conventional methods, e.g. centrifugation.

Alternatively, the aqueous suspension of nedocromil sodium partitioned between an aqueous phase and a liposome phase, may be concentrated, e.g. by centrifugation, ultrafiltration or dialysis, to give a liposome gel. This gel may be used in several ways, e.g. it may be incorporated in an ointment base, resuspended in or an isotonic, buffered saline solution, which may optionally contain nedocromil sodium. Such formulations may be made up from the liposome gel, and suitable excipients immediately prior to use.

The compositions according to the invention are advantageous in that they are more efficacious, produce less side effects, are longer acting, less toxic, distributed in the body tissues in a different manner or have other advantageous properties when compared to other similar compositions.

The dosage given will vary with the particular compositions used, the condition to be treated and its severity. We prefer to use an effective amount of nedocromil sodium liposomes, e.g. for inhalation treatment of reversible obstructive airways disease, from 0.01 to 50 mg in the treatment of these conditions, preferably from 0.01 to 30 mg, more preferably from 1 to 20 mg and most preferably from 10 to 20 mg.

We further provide a method of treatment of the above mentioned conditions, e.g. reversible obstructive airways disease, which comprises administration of a therapeutically effective amount of a composition as hereinbefore described.

GENERAL PROCEDURE FOR PREPARING NEDOCROMIL SODIUM CONTAINING LIPOSOMES

The desired quantity (e.g. 250 mg) of the appropriate phospholipid or mixture of phospholipids (e.g. egg lecithin, DTPC, DHPC or DOPC), together if desired with any other lipid soluble components (e.g. cholesterol, cholesterol stearate) is weighed into a round bottom flask. The lipid component is dissolved in a small quantity (c. 60 ml) of a suitable solvent (e.g. ethanol), and evaporated to dryness under reduced pressure using a rotary film evaporator, to leave a thin film of phospholipid on the inner surface of the flask.

An aqueous solution of nedocromil sodium of appropriate concentration (e.g. 80 mg/ml) is prepared by dissolving a weighed amount of nedocromil sodium in 20 ml of an aqueous medium (e.g. 0.9% w/v saline solution, buffer solution, etc) and if desired the pH of the resulting solution is lowered. The aqueous solution of the nedocromil sodium is warmed to a temperature 20° C. above the phase transition temperature of the lipid(s), added to the lipid film in the flask, and the flask gently shaken until all the lipid film is dispersed. The resulting suspension contains liposomes ranging from 200 nm to 10 μm in size.

The suspension is allowed to equilibrate for 48 hours, at 37° C.

These suspensions contain nedocromil sodium partitioned between the free aqueous phase and the liposome phase.

After 24 hours the suspension, in most cases, separates out to form a colloidal precipitate, which is readily redispersed on shaking.

The following nedocromil sodium liposomes compositions were prepared using the above general procedure:

| | |
|---|---|
| 1. DHPC | 260 mg |
| Nedocromil sodium | 800 mg |
| 0.9% w/v saline solution | 10 ml |
| 2. DHPC | 520 mg |
| Cholesterol stearate | 280 mg |
| Nedocromil sodium | 800 mg |
| Demineralised water | 5 ml |
| 3. DHPC | 260 mg |
| Cholesterol | 140 mg |
| Nedocromil sodium | 800 mg |
| Demineralised water | 10 ml |
| 4. DHPC | 260 mg |
| Nedocromil sodium | 800 mg |
| 0.9% w/v saline solution | 10 ml |
| 5. DHPC | 260 mg |
| Nedocromil sodium | 800 mg |
| 150 mM potassium chloride | |
| 10 mM Tris buffer, pH 7.4 | 10 ml |
| in water | |
| 6. DHPC | 180 mg |
| DTPC | 80 mg |
| Nedocromil sodium | 800 mg |
| 0.9 w/v saline solution | 10 ml |
| 7. DHPC | 260 mg |
| Nedocromil sodium | 800 mg |
| Cetylpyridinium chloride | 80 mg |
| 0.9 w/v saline solution | 10 ml |
| 8. Egg lecithin | 260 mg |
| Nedocromil sodium | 800 mg |
| Demineralised water | 10 ml |
| 9. Egg lecithin | 520 g |
| Nedocromil sodium | 1.6 g |
| Demineralised water | 10 ml |
| 10. DTPC | 130 g |
| Nedocromil sodium | 400 mg |
| 0.9% w/v saline solution | 10 ml |
| 11. DTPC | 130 mg |
| Nedocromil sodium | 800 mg |
| 0.9% w/v saline solution | 20 ml |
| 12. DTPC | 260 mg |
| Nedocromil sodium | 800 mg |
| 0.9% w/v saline solution | 10 ml |
| 13. DTPC | 260 mg |
| Nedocromil sodium | 800 mg |
| 0.9% w/v saline solution | 10 ml |
| 14. DTPC | 520 g |
| Nedocromil sodium | 1.6 g |
| 0.9% w/v saline solution | 160 ml |
| 15. DOPC | 260 mg |
| Nedocromil sodium | 800 mg |
| Demineralised water | 10 ml |
| 16. DTPC | 260 mg |
| Cholesterol stearate | 140 mg |
| Nedocromil sodium | 800 mg |
| Demineralised water | 10 ml |

DETERMINATION OF PERCENTAGE NEDOCROMIL SODIUM ASSOCIATED WITH LIPOSOMES

The equilibrated, nedocromil sodium liposome dispersion is centrifuged at 70,000 G for one hour. Aliquots of the supernatant are assayed in an ultraviolet spectrophotometer, at 326 nm, to determine concentration of free nedocromil sodium.

The percentage of nedocromil sodium associated with the liposomes is determined from the relationship: percentage nedocromil sodium (nedocromil) associated with liposome=

$$\frac{[\text{Total of nedocromil}] - [\text{nedocromil in supernatant}]}{[\text{Total nedocromil}]} \times 100$$

RATE OF NEDOCROMIL SODIUM RELEASE FROM LIPOSOMES, AND LIPOSOME HALF-LIFE

The rate of nedocromil sodium release from the liposomes may be determined by centrifuging the nedocromil sodium liposomes at 70,000 G as above, discarding the supernatant and resuspending in isotonic saline, buffered at pH 7.4. Aliquots of the resuspended liposomes, agitated at 37° C., were centrifuged at intervals, and the concentration of nedocromil sodium in the supernatant determined by u.v. spectrophotometry. The release constant, k, of the liposome is determined by plotting ln [nedocromil released] v time The half-life of the liposome, $t_{178}$, is given by the £ ½ relationship $$t_{\frac{1}{2}} = \frac{\ln 2}{k}$$

Liposome half lives may also be determined using the dilution method described by M Ahmed et al, Biochemical Pharmacology, 29, 2361–2365, (1980).

DETERMINATION OF FLUX AND PERMEABILITY COEFFICIENT PREPARATION OF MEMBRANES

Albino hairless mice of either sex and aged 10 to 12 weeks were sacrificed by cervical dislocation and the dorsal skin removed with the minimum of handling. Any subcutaneous fat, visible as discrete globules, was removed. The skin samples were examined for any signs of damage before use. One skin sample was used per diffusion cell and was mounted, epidermal side up, over the opening in the upper section of the diffusion cell and was then secured with an 'O' ring. Excess skin was trimmed away before assembly of the cell.

DIFFUSION CELL ASSEMBLY

A small amount of silicone grease was applied to the 'O' ring of the upper section after securing the membrane. The upper section was then pushed firmly into the lower chamber until correctly positioned. The chamber was then filled with saline pre-equilibrated to 37°. The volume of each cell was adjusted individually to ensure that the skin membrane remained level. The fill volume was then marked on the sidearm.

EXPERIMENTAL PROCEDURE

The set of eight diffusion cells were mounted on a carrier plate held in a thermostatically controlled water bath set at 37° and were allowed to equilibrate. Each cell was positioned over an underwater magnetic stirrer motor and the water level was adjusted to be approximately the same as the skin surfaces. This ensured that the temperature of the skin surface remained at 30°.

The vehicle to be studied was applied, either by delivery from a micropipette. The preparation was then evenly distributed over the exposed skin surface using a small glass rod. The weight of each aliquot applied was determined by accurately weighing at least 10 samples delivered by the micropipette or syringe.

Following application of the vehicle the magnetic stirrers were switched on and at appropriate time invervals 1.0 ml samples of the receptor fluid were removed via the side arms and immediately replaced with fresh saline pre-equilibrated to 37°. The samples were then deep frozen until analysed for the drug by High Performance Liquid Chromatography (HPLC).

At least three replicate diffusion cells were used for each formulation studied.

DATA HANDLING

Assuming that only passive diffusion occurs during the transport of the drug across the skin, the rate of penetration can be given by Fick's law.

$$J = P\Delta C$$

Where

J is the flux, the amount of drug diffusing per unit area per unit time,

P is the permeability coefficient $\Delta C$ is the concentration difference across the stratum corneum.

INITIAL CONCENTRATION VS ENTRAPMENT

The entrapment ratio of nedocromil sodium was measured by conventional methods, e.g. measurement of total nedocromil sodium present and measurement of free nedocromil sodium.

| Initial concentration (% w/v) | % w/w |
|---|---|
| 4.0 | 23.4 |
| 8.0 | 37.5 |
| 16.0 | 37.8 |
| 16.0 | 38.8 |

What we claim is:

1. A pharmaceutical composition comprising an aqueous suspension containing nedocromil sodium partitioned between a free aqueous phase and a liposome entrapped phase.

2. A pharmaceutical composition according to claim 1 wherein the entrapment ratio of nedocromil sodium is from 0.1 to 50% w/w nedocromil sodium/lipid.

3. A pharmaceutical composition according to claim 1 wherein the concentration of the entrapped aqueous nedocromil sodium solution is from 0.1% to 40% w/v.

4. A pharmaceutical composition according to claim 1 comprising an aqueous suspension of liposomes wherein the concentration of liposomes is from 5% to 80% w/v.

5. A pharmaceutical composition according to claim 1 comprising an aqueous solution of nedocromil sodium substantially entrapped in a liposome phase having a total concentration of from 0.01% to 30% w/v.

6. A composition according to claim 1 wherein the liposomes have a diameter of from 100 $\mu$m to 10 $\mu$m.

7. A composition according to claim 1 wherein the liposomes comprise one or more natural or synthetic lecithins.

8. A process for the manufacture of a composition according to claim 1 which comprises dispersing a thin film of a lipid in an aqueous solution of nedocromil sodium.

9. A method of treatment of reversible obstructive airways disease which comprises administration of a therapeutically effective amount of a pharmaceutical composition according to claim 1.

* * * * *